(12) United States Patent
Bullock et al.

(10) Patent No.: US 9,089,865 B2
(45) Date of Patent: Jul. 28, 2015

(54) ATOMIZER DEVICE HAVING A DISPOSABLE NOZZLE

(75) Inventors: John K. Bullock, Houston, TX (US); G. Allen Allred, Salt Lake City, UT (US); Jeff Bullock, Eagle Mountain, UT (US)

(73) Assignee: Alcove Medical, Inc., Eagle Mountain, UT (US)

( * ) Notice: Subject to any disclaimer, the term of this patent is extended or adjusted under 35 U.S.C. 154(b) by 722 days.

(21) Appl. No.: 13/369,401

(22) Filed: Feb. 9, 2012

(65) Prior Publication Data

US 2013/0206866 A1    Aug. 15, 2013

(51) Int. Cl.
*A62C 5/02*     (2006.01)
*B05B 15/06*    (2006.01)
*A61M 11/02*    (2006.01)
*B05B 7/24*     (2006.01)
*A61M 11/00*    (2006.01)
*A61M 11/06*    (2006.01)
*B05B 15/00*    (2006.01)

(52) U.S. Cl.
CPC ............ *B05B 15/065* (2013.01); *A61M 11/003* (2014.01); *A61M 11/02* (2013.01); *B05B 7/2424* (2013.01); *B05B 15/066* (2013.01); *A61M 11/06* (2013.01); *B05B 15/008* (2013.01); *Y10T 29/49826* (2015.01)

(58) Field of Classification Search
CPC .. B05B 15/065; B05B 15/008; B05B 15/066; B05B 7/2424; Y10T 29/49826; A61M 11/02; A61M 11/06; A61M 11/003
USPC ............ 239/8, 318, 337, 340, 344, 346–349, 239/354, 369, 375, 526, 530–532, 600
See application file for complete search history.

(56) References Cited

U.S. PATENT DOCUMENTS 1,097,008 A * 5/1914 DeVilbiss ...................... 222/484
6,021,961 A * 2/2000 Brown ........................... 239/398

* cited by examiner

*Primary Examiner* — Christopher Kim
(74) *Attorney, Agent, or Firm* — David R. Conklin; Kirton McConkie (57) ABSTRACT

An atomizer device for use in discharging a liquid into or on the body of the patient, the device having reusable and disposable components designed to safely and automatically prevent pathogens contamination.

12 Claims, 12 Drawing Sheets

ATOMIZER DEVICE HAVING A DISPOSABLE NOZZLE

BACKGROUND OF THE INVENTION

The present invention relates generally to atomizer devices for use in discharging a liquid into or on the body of a patient. More particularly, the present device relates to an atomizer device having reusable and disposable components designed to safely and automatically prevent contamination of a medication contained in a medicament container attached to the atomizer device.

Atomizer devices have been in use for many years in order to create a spray from a reservoir of a liquid. Early atomizer devices included a receptacle or container for a liquid that was attached to a gas tube and a liquid tube. The gas tube and the liquid tube communicated at their outward ends with a common spray head. A venturi effect was created by the spray head such that liquid was withdrawn from the receptacle through the liquid tube as gas was passed through the gas tube, thereby forming a spray discharged from the atomizer.

Modern, single-use atomizer devices have been provided which include a means for holding a liquid, such as a container, and atomizing nozzle in communication with a liquid holding means, and a means for supplying a compressed gas, such as gas or oxygen, to the atomizing nozzle, as taught in the U.S. Pat. No. 6,021,766, which is incorporated herein by reference. Modern single-use atomizers include a unitary device comprised of disposable materials, wherein the entire atomizer device is discarded following use of the device on a patient. In this way, cross-contamination and related spreading of sickness and disease between patients is prevented. Further, the clinician is able to avoid the time-consuming process of cleaning and sterilizing a non-disposable atomizer unit.

In practice, only certain portions of the single-use atomizers are subjected to patient contamination. For example, patient contamination often occurs through aspiration or backflow of the patient's nasal contents or saliva with portions of the atomizer which come into contact with the patient. However, current atomizer devices require disposal of the entire device, thereby increasing the cost of making and using the device.

Accordingly, there is a need for an improved disposable atomizer device for medical use that overcomes or avoids the problems of prior disposable atomizer devices. Such an atomizer device is disclosed herein.

BRIEF SUMMARY OF THE INVENTION

The present invention relates generally to atomizer devices for use in discharging a liquid into or on the body of a patient. More particularly, the present device relates to an atomizer device having reusable and disposable components designed to safely and automatically prevent contamination of a medication contained in a medicament container attached to the atomizer device. The disposable nature of the present invention further prevents pathogens from being passed from one patient to another, wherein the reusable portion of the atomizer device is used between multiple patients.

In some implementations of the present invention, an atomizer device is provided having an atomizer body including a gas inlet tube, a liquid inlet tube, a nozzle receptacle and a nozzle latch. The atomizer device further includes a nozzle having a proximal end, a distal end, a gas outlet tube, and a liquid outlet tube, the proximal end of the nozzle being removably coupled to the nozzle receptacle of the atomizer body such that the nozzle latch of the atomizer body is selectively coupled to a catch of the nozzle, wherein the gas outlet tube is in fluid communication with the gas inlet tube, and a liquid outlet tube is in fluid communication with the liquid inlet tube. The atomizer device further includes a trigger assembly whereby to selectively enable passage of compressed gas through the gas inlet tube and the gas outlet tube. In some instances, the atomizer device includes an outlet valve, wherein air is diverted through the nozzle component by stopping air flow through the outlet valve.

In some implementations, the atomizer device further includes an atomizer nozzle in fluid communication with the gas outlet tube and the liquid outlet tube, wherein a liquid from the liquid outlet tube and a gas from the gas outlet tube are mixed in the atomizer nozzle to form an atomized solution. In some aspects of the present invention, the atomizer nozzle includes a venturi section wherein, by Bernoulli's principle, the liquid and gas are mixed in the venturi section prior to being passed through the atomizer nozzle.

Some aspects of the present invention include a disposable atomizer device having an atomizer body that is selectively coupled to a disposable nozzle component. The atomizer body includes a nozzle latch having a clip for compatibly retaining a catch or catch surface of the disposable nozzle component. In some implementations, the nozzle component further includes a nozzle or atomizer nozzle.

A nozzle component in accordance with the present invention may include any length, shape, structural integrity, or material as may be desired to facilitate application of a medicament or other liquid to a patient. For example, in some aspects a rigid nozzle component is provided. In other aspects, a flexible nozzle component is provided. Further still, in some implementations a nozzle component is provided having an extended length whereby to distance the position of an atomizer nozzle from the atomizer body of the atomizer device. In some aspects, a unitary nozzle component is provided. In other aspects, a modular nozzle component is provided.

In some implementations of the present invention, an atomizer device is provided having a trigger assembly. In some instances, trigger assembly includes a trigger valve system for providing controlled release of compressed gas to the nozzle of the nozzle component, the trigger valve system including a tapered needle valve positioned in a needle support surrounded by a valve housing within a cap, the needle valve slidably disposed in a valve channel in the valve housing and in substantially coaxial alignment with the gas outlet tube of the nozzle component, the valve housing having a pressure relief port in communication with the valve channel, the needle support being removably engaged within the cap for retaining the needle valve within the valve housing, the needle valve being resiliently biased towards the cap, wherein when the needle support is depressed inwardly, the needle support seals the pressure relief port while the needle valve releases the compressed gas to flow through the valve channel into the gas outlet tube and to the nozzle, thereby withdrawing the liquid into the nozzle via the liquid outlet tube such that the liquid is atomized when mixed with the compressed gas in the nozzle.

In some implementations, the atomizer body includes a component nozzle receptacle into which a proximal end of the nozzle component is removably inserted. The component nozzle receptacle may include a first nozzle receptacle and a second nozzle receptacle, wherein the first nozzle receptacle is configured to receive a proximal end of the liquid outlet tube of the nozzle component, and the second nozzle receptacle is configured to receive a proximal end of the gas outlet tube, the nozzle receptacle and the nozzle component forming a fluid tight seal.

In some implementations, the nozzle latch of the atomizer body is resilient, wherein the nozzle latch may be temporarily displaced to permit removal of the nozzle component from the atomizer body. Upon release of the nozzle latch, the latch's resilient nature enables the nozzle latch to resume its initial position.

In some aspects of the present invention, a method for manufacturing a disposable atomizer device is provided. This method includes a first step for providing an atomizer body having a proximal end, a distal end, and a container receptacle, the proximal end having a trigger assembly and a gas inlet, the distal end having a nozzle latch. The method further includes a step for providing a nozzle component having a proximal end and a distal end, the proximal end of the nozzle component being configured to couple to the distal end of the atomizer body, the proximal end of the nozzle component further comprising a catch configured to selectively couple with the nozzle latch, the distal end of the nozzle component further comprising a nozzle. In some instances, the nozzle component further includes a gas outlet tube in fluid communication with the gas inlet and a liquid outlet tube in fluid communication with a fluid container coupled to the container receptacle.

BRIEF DESCRIPTION OF THE SEVERAL VIEWS OF THE DRAWINGS

In order that the above-recited and other features and advantages of the invention are obtained and will be readily understood, a more particular description of the invention briefly described above will be rendered by reference to specific embodiments thereof, which are illustrated in the appended drawings. These drawings depict only typical embodiments of the invention and are not therefore to be considered to limit the scope of the invention.

FIG. 3, shown in parts A and B, is an exploded view of an atomizer device in accordance with a representative embodiment of the present invention.

FIG. 3, shown in parts C-G, show an atomizer device and an external trigger system in accordance with various representative embodiments of the present invention.

FIG. 4, shown in parts A and B, is a partially cross-sectioned detail view of an atomizer device in accordance with a representative embodiment of the present invention.

DETAILED DESCRIPTION OF THE INVENTION

The presently preferred embodiments of the described invention will be best understood by reference to the Figures, wherein like reference numbers indicate identical or functionally similar elements. It will be readily understood that the components of the present invention, as generally described and illustrated in the Figures, could be arranged and designed in a wide variety of different configurations. Thus, the following more detailed description, as represented in FIGS. 1 through 4B, is not intended to limit the scope of the invention as claimed, but is merely representative of some presently preferred embodiments of the invention.

The present disclosure describes systems and methods for providing an atomizer device having disposable components, thereby reducing the cost of the device and preventing cross-contamination between multiple patients. In particular, the present invention is directed to an atomizer device for directing a liquid into or onto the body of a patient, wherein certain portions of the atomizer device are reusable, and other portions of the atomizer device are disposable.

Figure 1:
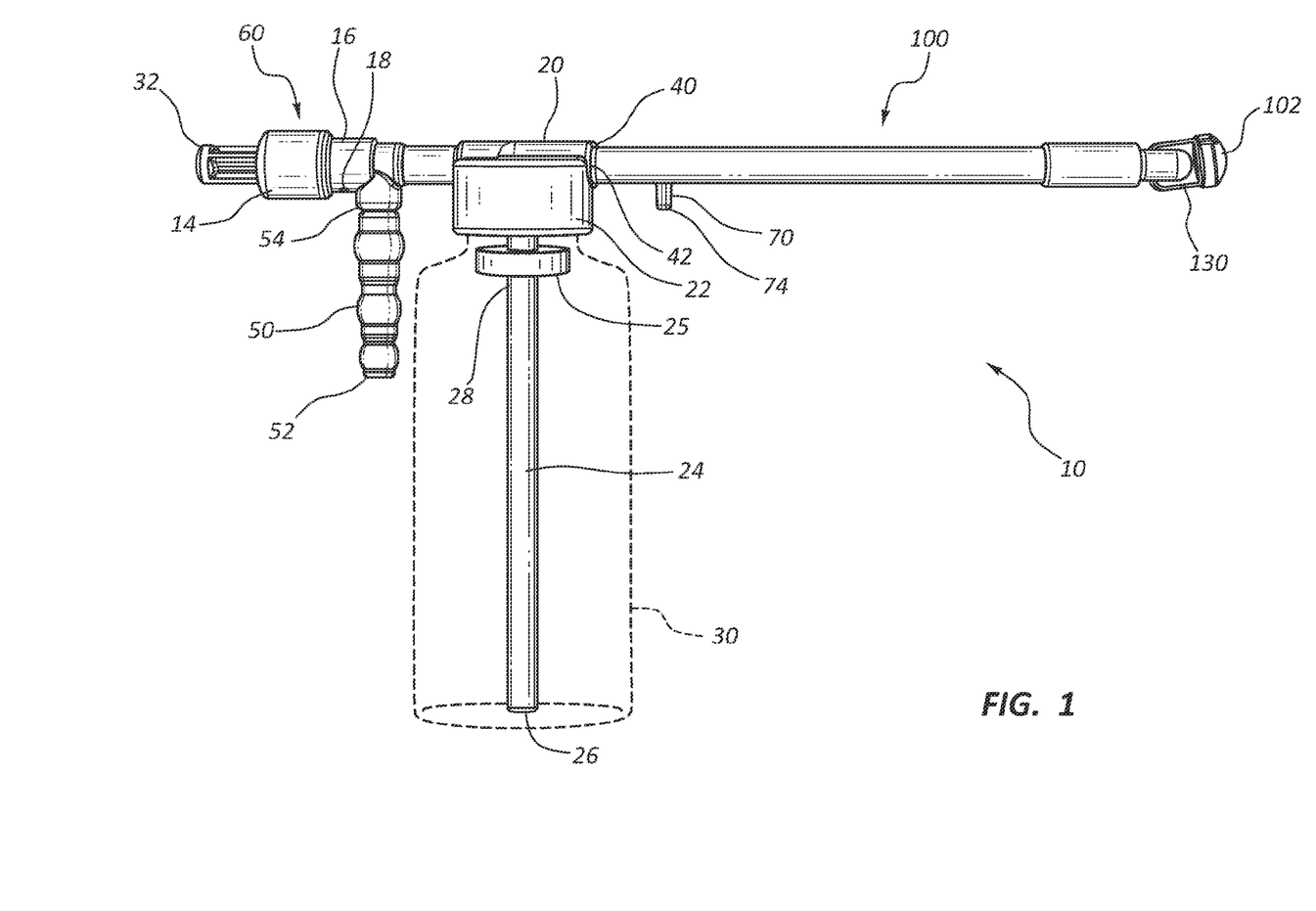
FIG. 1 is a side view of an atomizer device in accordance with a representative embodiment of the present invention.
Figure 2:
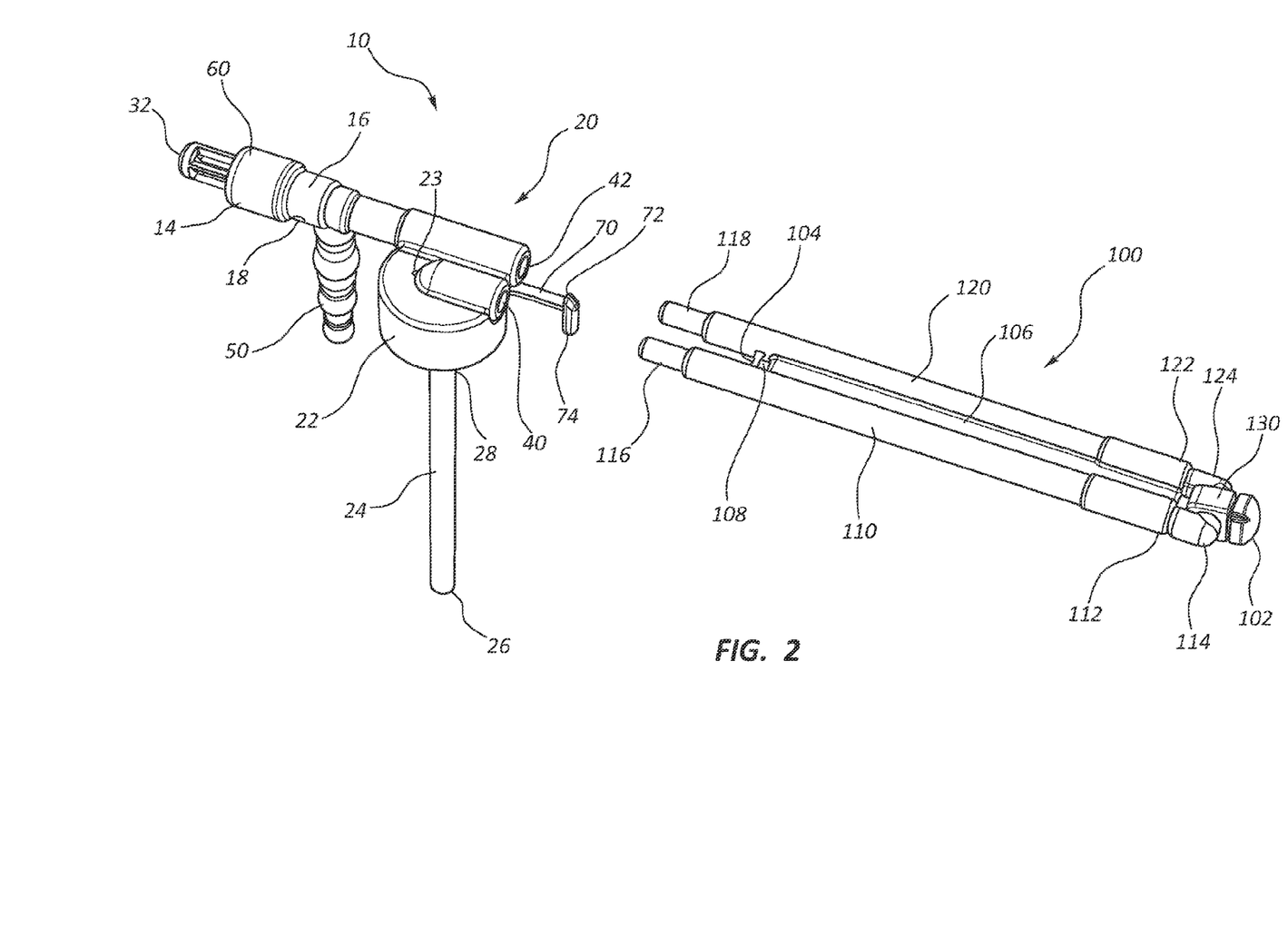
FIG. 2 is an isometric view of an atomizer body and nozzle component of an atomizer device in accordance with a representative embodiment of the present invention.

Referring now to FIGS. 1 and 2, an atomizer device 10 is shown. In some embodiments, an atomizer device 10 is provided which comprises a reusable atomizer body 20. Atomizer body 20 generally comprises a container receptacle 22 which is configured to receive a container 30. In some embodiments, container 30 comprises a fluid reservoir in which is stored a medicament or other liquid which is intended to be administered to the patient via atomizer device 10. Container receptacle 22 may further include a vent 23 which provides an airway between the fluid reservoir of container 30 and an exterior environment. Vent 23 facilitates pressure equilibrium between the fluid reservoir of container 30 and the exterior environment. Thus, vent 23 prevents pressure buildup within container 30. Further, in some embodiments vent 23 comprises a filter to prevent contamination of a medicament or other liquid stored in the fluid reservoir. For example, in some instances a filter is proved between inlet tube 24 and atomizer body 20 to prevent cross-contamination between fluid or medicament located within nozzle component 100 and uncontaminated fluid or medicament stored in container 30.

Atomizer body 20 further comprises a liquid inlet tube 24 having a distal end 26 which extends outwardly from atomizer body 20 and into container 30. A proximal end 28 of liquid inlet tube 24 is coupled to atomizer body 20 and terminates in a first nozzle receptacle 40. Thus, a fluid within container 30 is withdrawn via liquid inlet tube 24 and delivered to nozzle receptacle 40.

In some embodiments, liquid inlet tube 24 further comprises a check valve 25. Check valve 25 may include any device or system which prevents fluid and/or air from entering fluid reservoir of container 30 via liquid inlet tube 24. In some embodiments, check valve 25 comprises a duckbill valve. In other embodiments, check valve 25 comprises a ball valve.

Atomizer body 20 further comprises a gas inlet or gas inlet tube 50 for establishing fluid communication between atomizer body 20 and a source of compressed gas (not shown). Gas inlet tube 50 comprises a distal end 52 having features for retaining a compressed gas line. Gas inlet tube 50 further comprises a proximal end 54 that is coupled to atomizer body 20 and terminates in a second nozzle receptacle 42. Thus, compressed gas is delivered to second nozzle receptacle 42 via gas inlet tube 50.

In some embodiments, atomizer body 20 further comprises a trigger system 60 which forms a proximal end of atomizer body 20. Trigger system 60 is provided to enable a user to control passage of compressed gas between gas inlet tube 50 and second nozzle receptacle 42. In some embodiments, trigger system 60 merely comprises an opening, wherein gas is permitted to continuously flow through the opening until the opening is stopped by the user's finger or another suitable surface or device, whereupon the compressed gas is directed to the second nozzle receptacle 42. In other embodiments, trigger system 60 comprises a spring-loaded valve having a valve needle which blocks or permits passage of gas between gas inlet tube 50 and second nozzle receptacle 42, as taught in U.S. Pat. No. 6,021,766.

In particular, in some embodiments trigger system 60 comprises a trigger valve system including a tapered needle valve (not shown) positioned in a needle support 32 surrounded by a valve housing 16 within a cap 14, the needle valve being slidably disposed in a valve channel in the valve housing 16. The needle valve is substantially coaxially aligned within gas outlet tube 120 of nozzle component 100. Valve housing 16 further includes a pressure relief port 18 in communication with the valve channel. Needle support 32 is movably engaged within cap 14 and is configured to retain the needle valve with in valve housing 16. The needle valve is resiliently biased towards cap 14 via a spring (not shown).

Trigger system 60 is actuated by depressing needle support 32 inwardly, whereupon the needle support 32 seals pressure relief port 18 while the needle valve releases the compressed gas to flow through the valve channel into gas outlet tube 120 and to the atomizer nozzle 102. As this occurs, liquid from container 30 is withdrawn through liquid inlet tube 24 and delivered to atomizer nozzle 102 via liquid outlet tube 110. The liquid from liquid outlet tube 110 is atomized when mixed with the compressed gas from gas outlet tube 120.

In some embodiments, an external trigger system 140 having an air hose 142 attached to an air compressor 200 is directly coupled to gas inlet tube 50, as shown in FIGS. 3C-3G. External trigger system 140 comprises a hand grip having a trigger 144 which temporarily defeats an air valve within system 140. Upon defeating the air valve of trigger system 140, compressed air or gas from compressor 200 flows out of nozzle 146. Thus, in some embodiments external trigger system 140 replaces the function of trigger system 60.

In general, external trigger system 140 comprises an air sprayer having a nozzle 146 that is capable of being compatibly joined to gas inlet tube 50 of atomizer body 20. External trigger system 140 is further configured to permit single-handed operation. Trigger system 140 and nozzle 146 may comprise any configuration or shape which is compatible with atomizer body 20. For example, in some embodiments external trigger system 140 comprises a compressed air sprayer, such as those manufactured by ATMOS, Inc. In particular, in some embodiments external trigger system 140 comprises a compressed air sprayer which is part of an ATMOS ENT workstation or treatment cabinet. Further, external trigger system 140 may comprise an air gun having features for compatibly coupling to atomizer body 20.

Figure 3A:
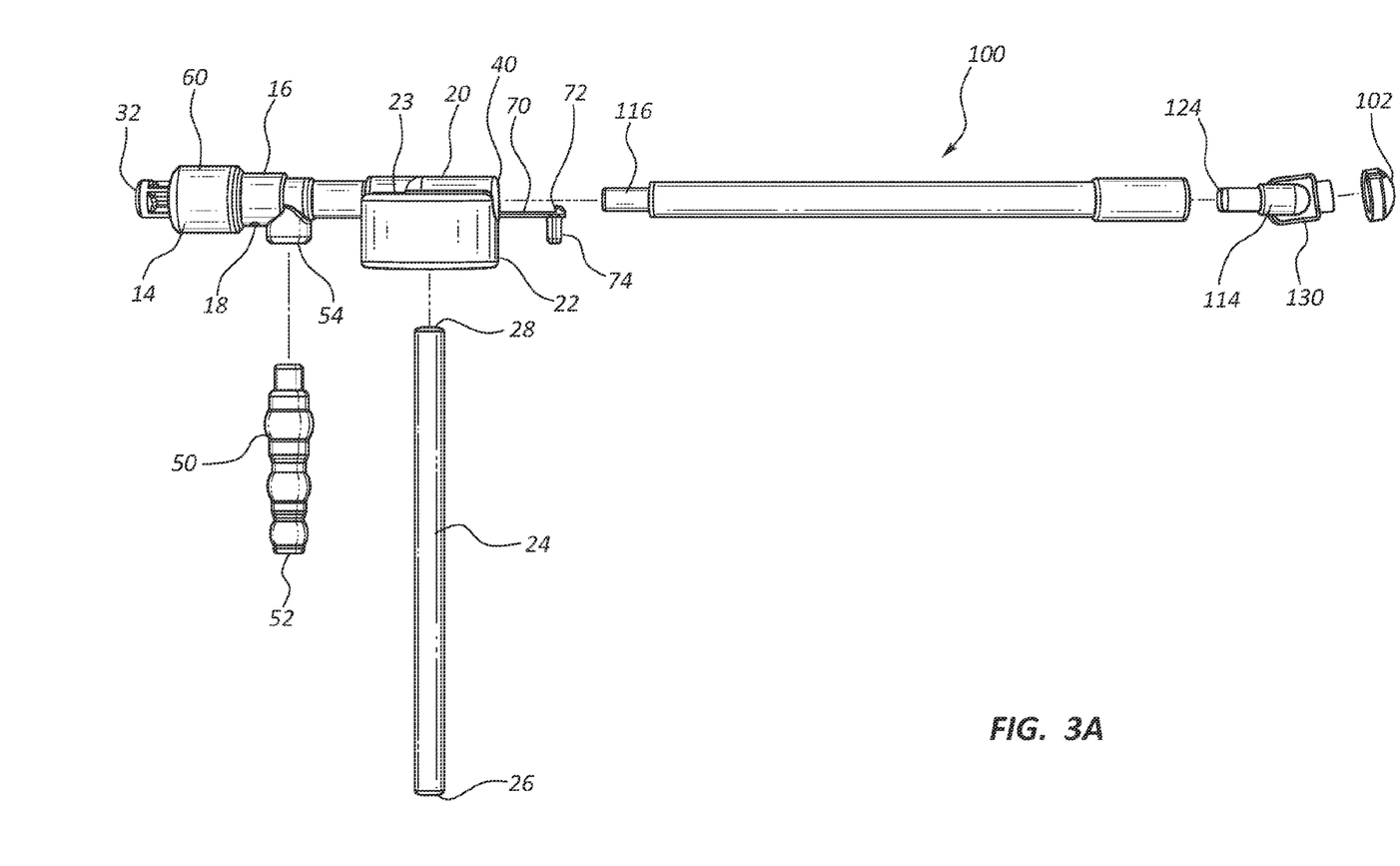
Figure 3B:
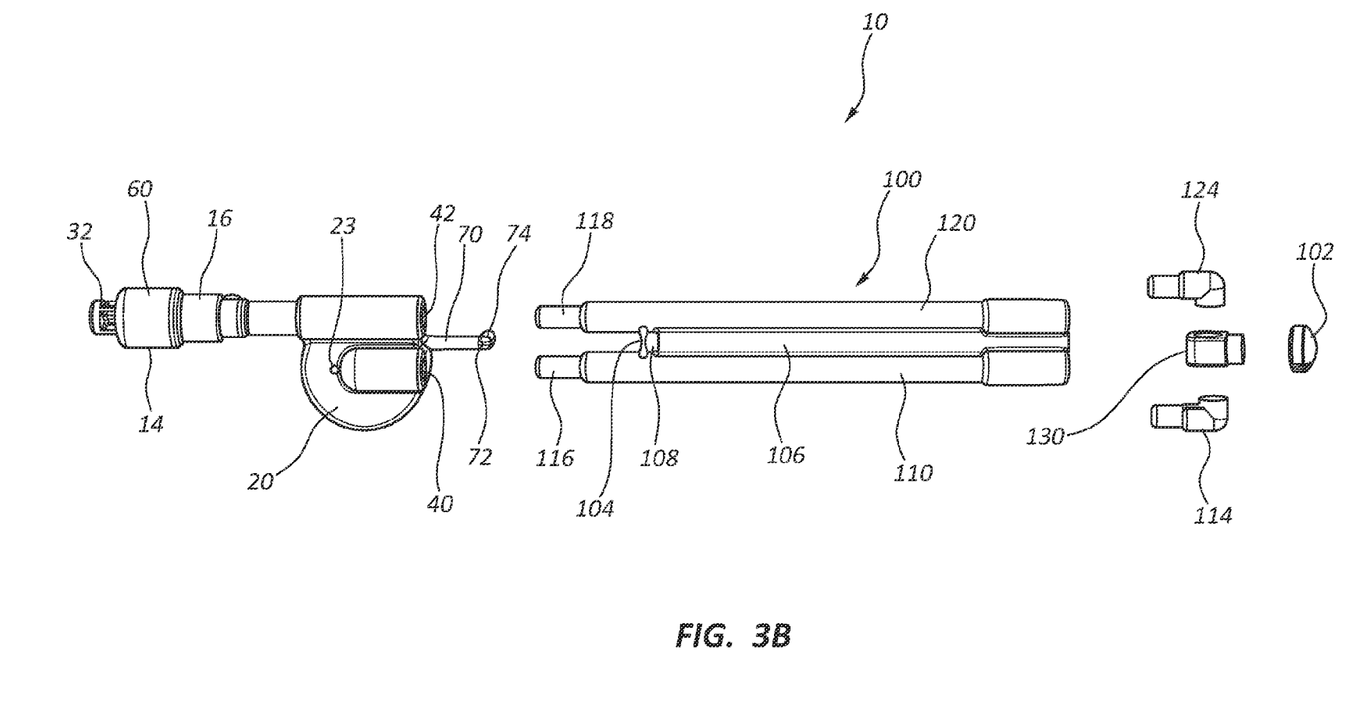
Figure 3C:
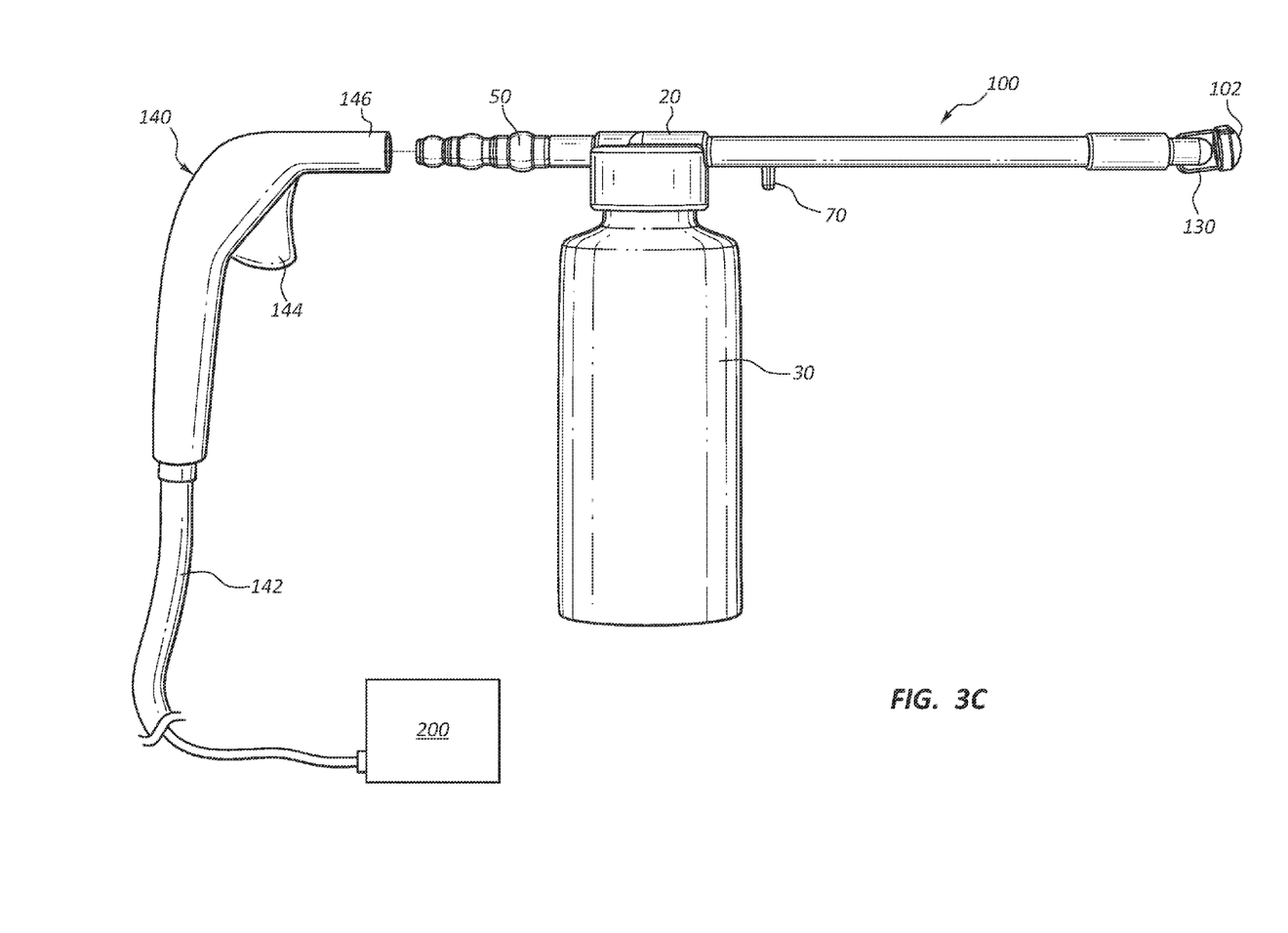
Figure 3D:
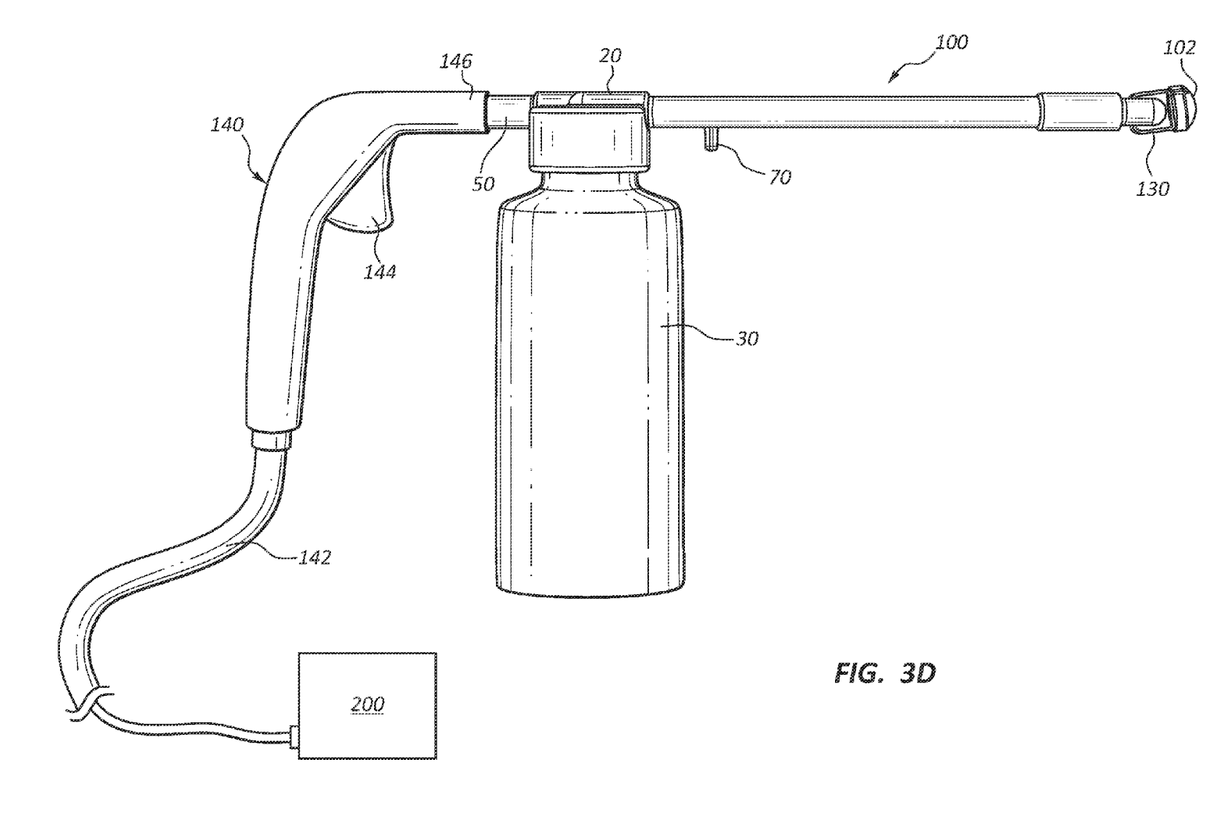

In some embodiments, the valve housing of atomizer body 20 is eliminated and replaced with gas inlet tube 50. In this configuration, external trigger system 140 may be attached directly to gas inlet tube 50 to permit single-handed operation, as shown in FIG. 3D.

In some embodiments, nozzle 146 is incompatible with gas inlet tube 50. Accordingly, an adapter 150 may be provided which comprises a first end 152 for compatibly coupling nozzle 146, and a second end 154 for compatibly coupling gas inlet tube 50, as shown in FIGS. 3E-3G.

Figure 3E:
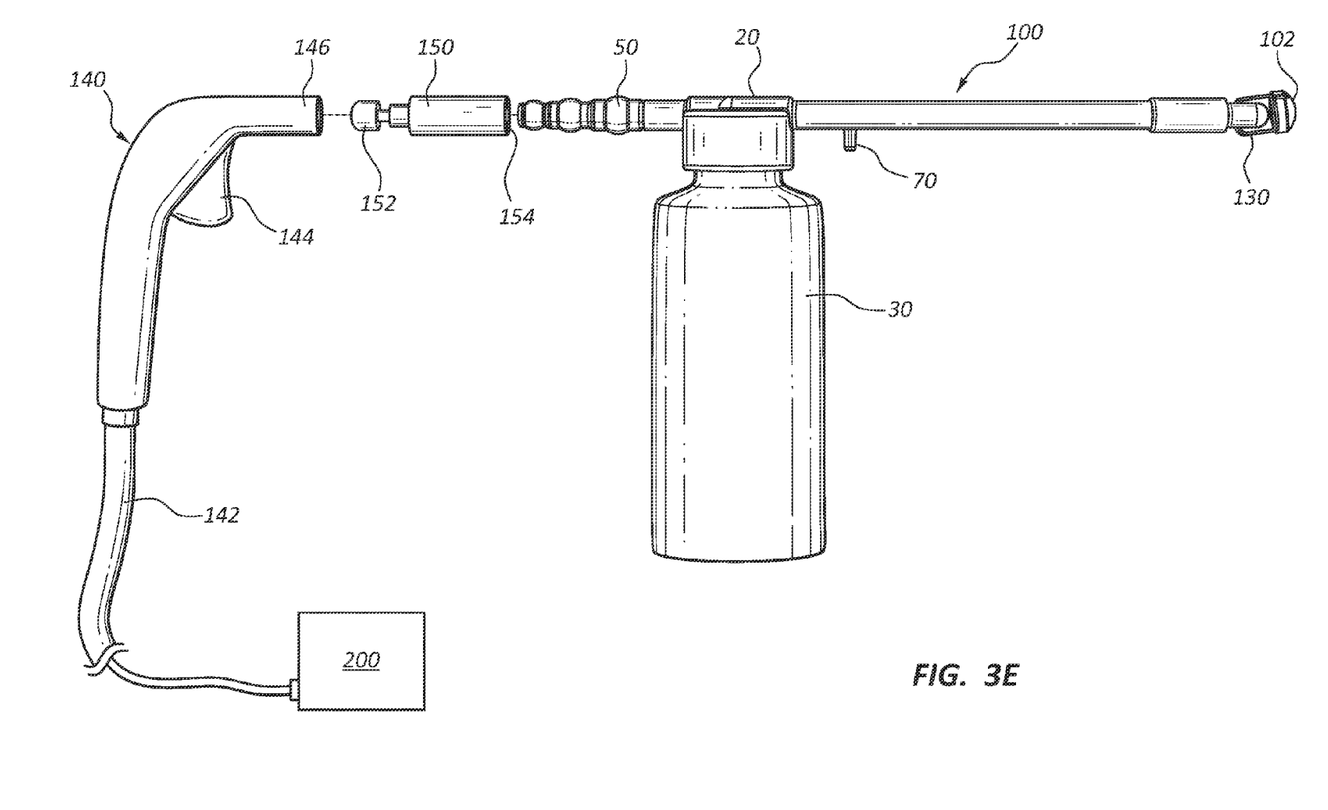
Figure 3F:
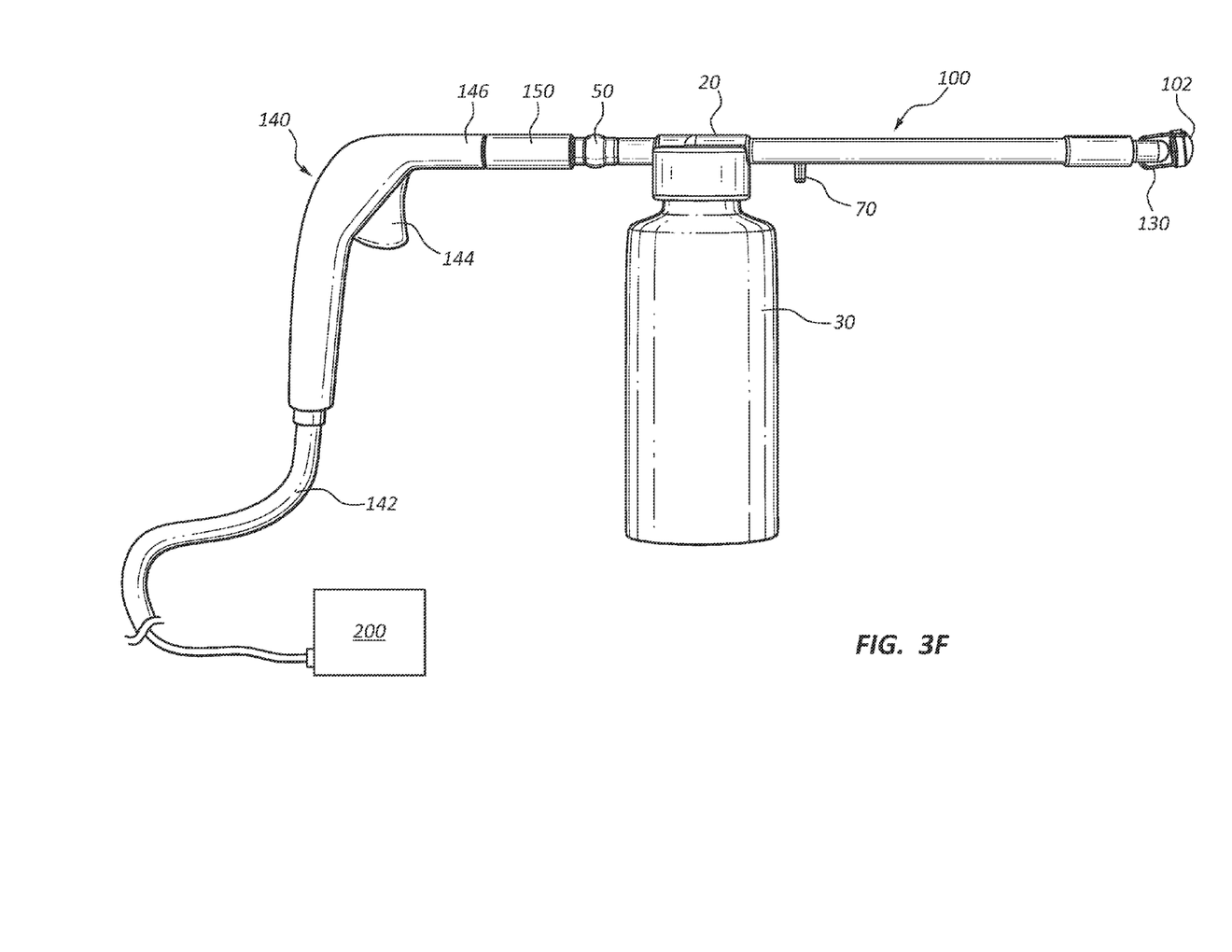
Figure 3G:
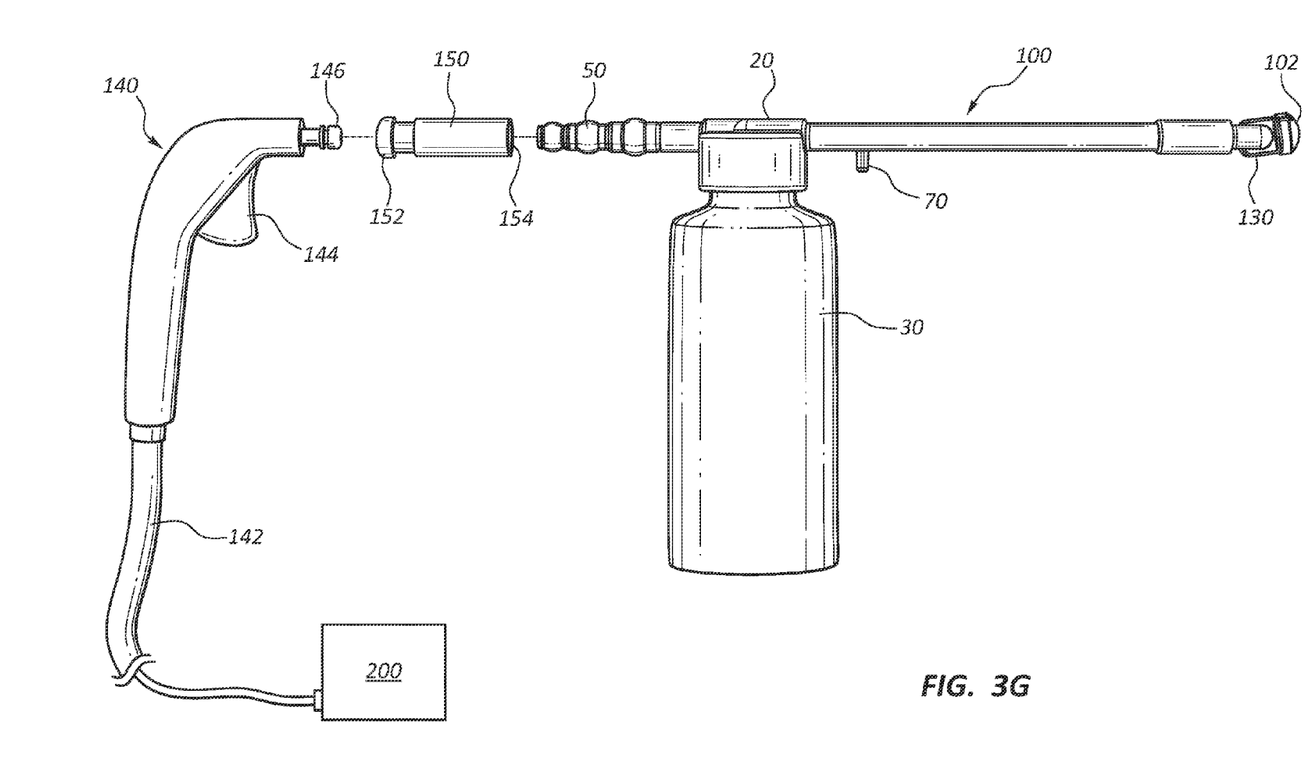

Referring now to FIG. 3E, in some embodiments first end 152 of adapter 150 comprises an outer surface that is configured to compatibly insert within nozzle 146. Second end 154 of adapter 150 further comprises an inner surface that is configured to compatibly receive gas inlet tube 50. Thus, adapter 150 permits coupling between external trigger system 140 and gas inlet tube 50, as shown in FIG. 3F Referring now to FIG. 3G, in some embodiments first end 152 of adapter 150 further comprises an inner surface that is configured to compatibly receive an outer surface of nozzle 146. The outer surface of first end 152 may further comprise features for receiving a second nozzle design (not shown), wherein a single adapter 150 may permit coupling between atomizer body 20 and various types, styles and/or brands of external trigger systems 140.

Figure 3H:
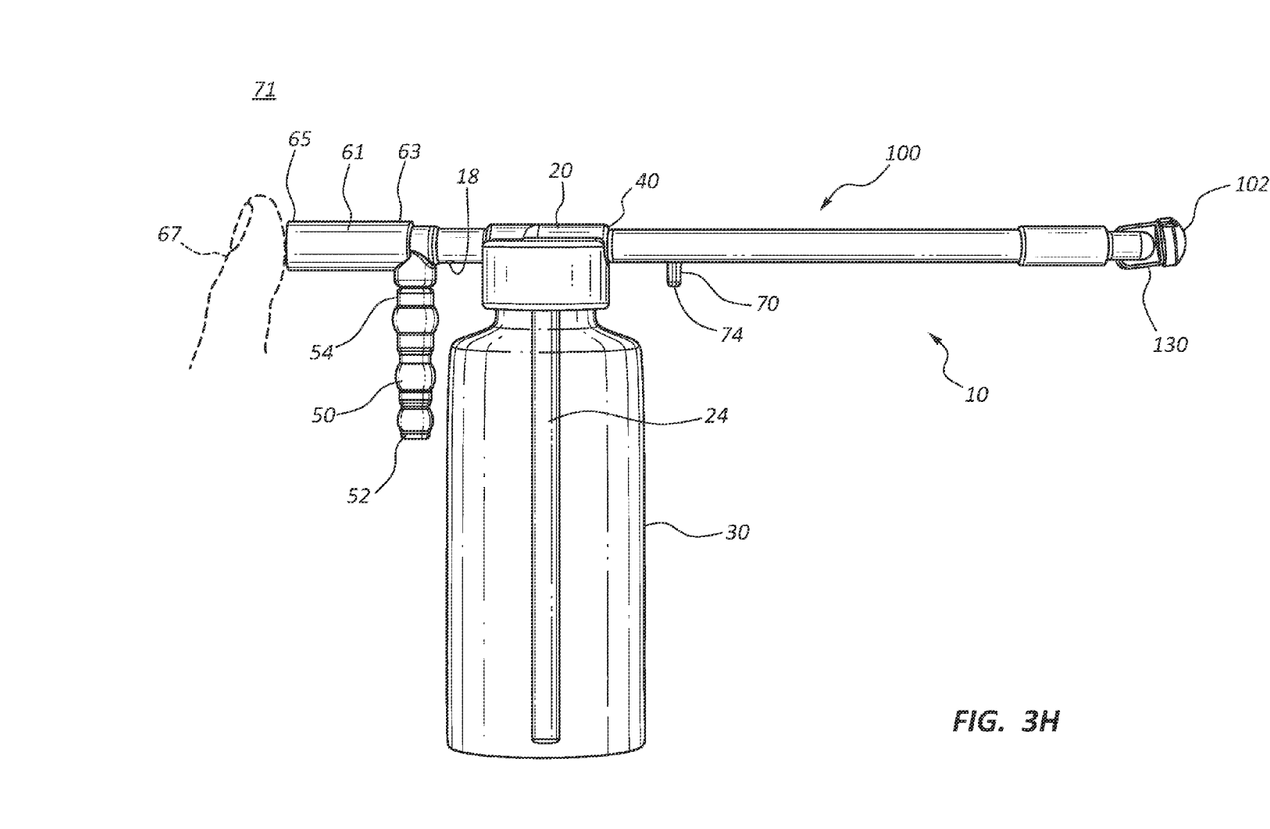
FIG. 3H shows an atomizer device having an outlet valve in accordance with a representative embodiment of the present invention.
Figure 4A:
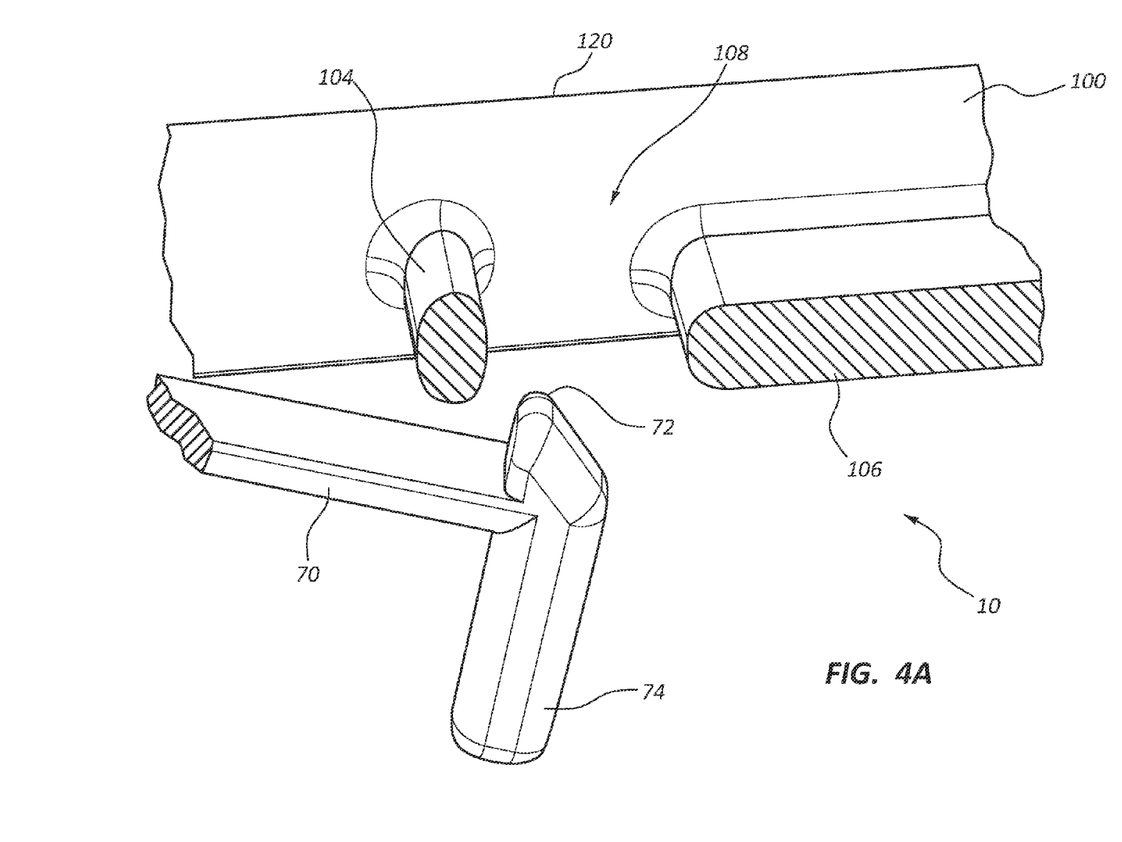
Figure 4B:
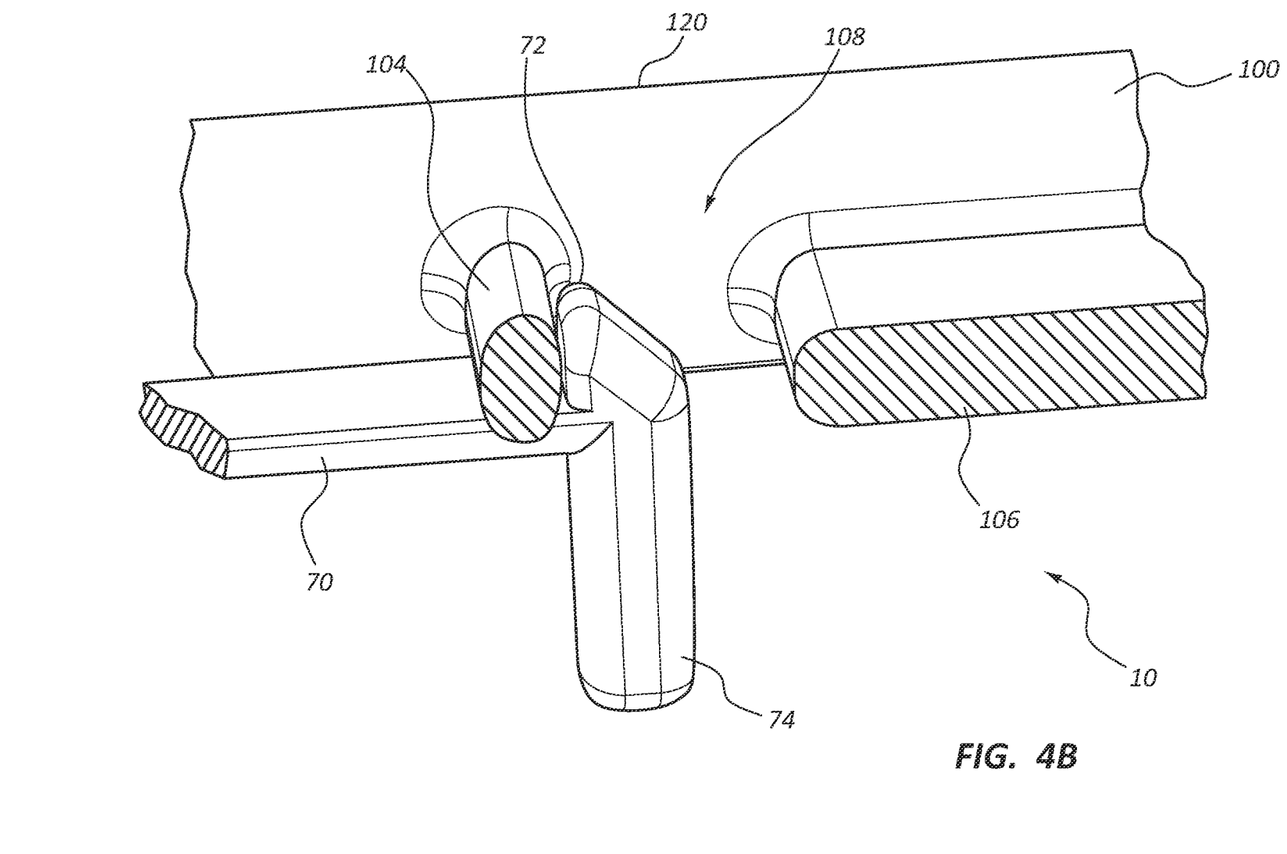

In some embodiments, atomizer body 20 further includes an outlet valve 61 comprising a tube in fluid communication with gas inlet tube 50 and nozzle component 100, as shown in FIG. 3H. In particular, outlet valve 61 comprises a first end 63 in fluid communication with gas inlet tube 50 and nozzle component 100, and a second end 65 in fluid communication with an exterior environment 71. In some embodiments, outlet valve 61 is provided in place of valve assembly 60 of the previous embodiments. Outlet valve 61 is configured to receive air from gas inlet tube 50 in preference over nozzle component 100. As such, compressed air introduced to atomizer device 10 via gas inlet tube 50 exits device 10 via second end 65 of outlet valve 61. However, when second end 65 of outlet valve 61 is stopped, the compressed air bypasses outlet valve 61 and flows through nozzle component 100. For example, in some embodiments second end 65 is stopped or blocked by the user's thumb 67. In other embodiments, second end 65 is stopped or blocked via a stopper or other mechanical device which prevents passage of air through send end 65.

Referring now generally to FIGS. 1-4B, atomizer body 20 further comprises a nozzle latch 70. Nozzle latch 70 generally comprises a flexible and resilient extension of atomizer body 20 which is configured to selectively couple and retain a disposable nozzle component 100 of atomizer device 10. As used herein, the terms "selectively couple" or "selectively coupled" denote any means, structures or methods whereby a user may choose to attach and detach disposable nozzle component 100 to atomizer body 20. Thus, the systems and methods of the present invention provide the user with flexibility in determining the interconnected relationship between nozzle component 100 and atomizer body 20.

In general, nozzle latch 70 provides a means whereby to selectively couple disposable nozzle component 100 to atomizer body 20. Accordingly, one having skill in the art will appreciate that the specific mechanics by which nozzle component 100 is selectively coupled to atomizer body 20 may be accomplished by any conceivable method or combination of methods.

For example, in some embodiments nozzle component 100 is selectively coupled to atomizer body 20 via a friction fit. In other embodiments, nozzle component 100 is selectively coupled to atomizer body 20 via a ball detent coupling. Further, in some instances nozzle component 100 is selectively coupled to atomizer body 20 via a keyed connection. Further still, in some instances nozzle component 100 is selectively coupled to atomizer body 20 via a threaded connection.

Disposable nozzle component 100 is provided as a means for mixing compressed gas from gas inlet tube 50 and a liquid from liquid inlet tube 24 to produce an atomized solution at atomizer nozzle 102. Accordingly, nozzle component 100 comprises a liquid outlet tube 110 and a gas outlet tube 120, wherein a proximal end 116 of liquid outlet tube 110 is configured to couple to first nozzle receptacle 40 and a proximal end 118 of gas outlet tube 120 is configured to couple to second nozzle receptacle 42.

In some embodiments, nozzle component 100 is further provided as a means for extending the position of atomizer nozzle 102 relative to atomizer body 20. Nozzle component 100 may comprise any length necessary to achieve use of the device in accessing areas of the patient requiring treatment. In some embodiments, nozzle component 100 is rigid. In other embodiments, nozzle component 100 is flexible, or semi flexible thereby enabling a user to position or reposition nozzle component 100 to achieve a desired configuration.

Nozzle component 100 further comprises a catch 104 which extends between liquid outlet tube 110 and gas outlet tube 120. Nozzle component 100 may further include a webbing 106 or other means whereby to link liquid outlet tube 110 and gas outlet tube 120 along their respective lengths. In some embodiments, a gap 108 is provided between catch 104 and webbing 106. Gap 108 is provided as a space for receiving clip 72 of nozzle latch 70. Accordingly, an interaction between clip 72 and catch 104 secures nozzle component 100 and atomizer body 20 during use of atomizer device 10.

One having skill in the art will appreciate that clip 72 may include any structure or features desired to facilitate selective coupling between nozzle component 100 and nozzle latch 70. For example, where nozzle component 100 is coupled to atomizer body 20 via a ball detent coupling, nozzle latch 70 may comprise a detent and clip 72 may comprise a ball. This connection may also include an air compressor fitting, wherein the nozzle latch 70 and clip 72 comprise interconnecting elements or components of the fitting. Similarly, where nozzle component 100 is coupled to atomizer body 20 via a friction fit, nozzle latch 70 may comprise an inner surface of an opening of atomizer body 20 and clip 72 may comprise an outer surface of nozzle component 100 that fits inside the opening of atomizer body 20. Accordingly, in a general sense nozzle latch 70 and clip 72 represent structures whereby a user by selectively couple nozzle component 100 to atomizer body 20.

Liquid outlet tube 110 and gas outlet tube 120 further comprise distal ends 112 and 122, respectively, which terminate into a venturi section 130. Venturi section 130 further comprises atomizer nozzle 102, wherein liquid outlet tube 110, gas outlet tube 120, and atomizer nozzle 102 are in fluid communication via venturi section 130. As the velocity of a gas increases through venturi section 130, pressure within liquid outlet tube 110 decreases thereby drawing liquid from container 30, through liquid inlet tube 24 and liquid outlet to 120, and into venturi section 130, wherein the liquid and gas mix to form the desired atomized solution. Upon release or deactivation of trigger system 60, the initial negative pressure within liquid outlet tube 110 returns to atmospheric pressure thereby preventing any unused liquid within disposable nozzle component 100 from returning to container 30.

In some embodiments, venturi section 130 and atomizer nozzle 102 are pivotally attached to distal ends 112 and 122 of liquid outlet tube 110 and gas outlet tube 120 via tubular elbows 114 and 124. Venturi section 130 and atomizer nozzle 102 are therefore capable of pivoting relative to the stationary position of outlet tubes 110 and 120. An exploded side view of atomizer device 10 is shown in FIG. 3A. An exploded top view of atomizer device 10 is shown in FIG. 3B.

In some embodiments, proximal ends 116 and 118 of liquid outlet tube 110 and gas outlet tube 120 further comprise a reduced outer diameter. As such, proximal ends 116 and 118 are compatibly inserted into first and second nozzle receptacles 40 and 42, respectively. In some embodiments, proximal ends 116 and 118 are individually keyed to fit into their respective nozzle receptacles 40 and 42. Proximal ends 116 and 118 may also comprise different lengths thereby preventing improper insertion of nozzle component 100 into atomizer body 20. Further still, in some embodiments proximal ends 116 and 118 are keyed to ensure a proper matching of nozzle component 100 to a compatible atomizer body 20.

For example, in some embodiments a first atomizer body is configured to be paired with a first nozzle component, and a second atomizer body is configured to be paired with a second nozzle component, wherein the first nozzle component is incompatible with the second atomizer body, and the second nozzle component is incompatible with the first atomizer body. Accordingly, a keyed connection between the first nozzle component and first atomizer body prevents improper paring of second nozzle component with first atomizer body. In other embodiments, a universal nozzle component is provided which is compatible with more than one type or style of atomizer body. As such, the proximal ends of the universal nozzle component are keyed to enable the universal nozzle component to be paired with any atomizer body. Similarly, in some instances a universal atomizer body is provided which is compatible with more than one type or style of nozzle component. Thus, the nozzle receptors of the universal atomizer body are keyed to enable the universal atomizer body to receive any nozzle component.

Following usage of atomizer device 10 in treating a first patient, nozzle component 100 may be removed from atomizer body 20 and disposed. Nozzle component 100 is removed from atomizer body 20 by manipulating handle 74 of nozzle latch 70 such that clip 72 of nozzle latch 70 is disengaged from catch 104 of nozzle component 100, as shown in FIG. 4A. A new nozzle component 100 may then be inserted into atomizer body 20 by again manipulating handle 74 of nozzle 70 such that clip 72 does not obstruct insertion of nozzle component 100 into first and second nozzle receptacles 40 and 42 of atomizer body 20. Once the new nozzle component 100 is fitted within atomizer body 20, handle 74 of nozzle at 70 is released thereby allowing clip 72 to engage catch 104 of nozzle component 100, as shown in FIG. 4B. The newly installed nozzle component 100 may then be used to treat a second patient without fear of cross-contamination between the first and second patients.

Some embodiments of atomizer device 10 are configured to safely and automatically prevent contamination of the medicaments contained in the attached container 30. Specifically, venturi 130 and atomizer nozzle 102 are designed to allow a significant vacuum to be produced in atomizer nozzle 102 when a stream of compressed gas passes through air outlet tube 120 during use of the device 10. This strong negative pressure is designed to withdraw fluid from container 30 through liquid inlet tube 24, the fluid being delivered to venturi 130 via liquid outlet to 110 and tubular elbow 114. When the gas flow is stopped (i.e.: trigger system 60 is deactivated), the negative pressure is immediately ended thereby returning to atmospheric pressure and causing no further liquid to be dispensed. Any liquid remaining in atomizer nozzle 102 is removed with nozzle component 100 as it is discarded. In this way, the disposable nature of nozzle component 100 ensures that pathogens are prevented from contaminating the unused medicaments remaining in container 30 via liquid inlet tube 24.

In some aspects of the present invention, nozzle component 100, tubular elbows 114 and 124, venturi 130 and atomizer nozzle 102 comprise a unitary disposable unit. In other aspects, nozzle component 100 comprise a modular unit having various parts which may be removed and/or interchanged as desired to prevent cross-contamination between patients and/or medicaments intended for patient use. Accordingly, in some embodiments nozzle component 100 is removed from atomizer body 20 in its entirety following use of atomizer device 10. In other embodiments, a portion of nozzle component 100 is removed following use of atomizer device 10, such as atomizer nozzle 102.

Nozzle component 100 may further include an antimicrobial coating or surface to further prevent contamination or infection to the patient. Nozzle component 100 may further include a marking to indicate that the component is intended for single patient use. In some embodiments, nozzle component 100 is stored in a protective packaging or enclosure prior to use. For example, nozzle component 100 may be sterilized prior to being packaged in a sterile packaging. A user accesses nozzle component 100 by removing nozzle component 100 from the packaging, attaches nozzle component 100 to atomizer body 20 of atomizer device 10, and then use atomizer device 10 to treat a patient. Following use of the device 10, the user removes nozzle component 100 from atomizer body 20 and disposes nozzle component 100, as previously discussed. In some embodiments, atomizer body 20 may further be disposed following prolonged use of atomizer device 10. In other embodiments, atomizer body 20 may be autoclaved or otherwise sterilized to permit further use.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. An atomizer device, comprising:
   an atomizer body having a proximal end, a distal end, and a container receptacle for receiving a container, the proximal end having a trigger assembly and a gas inlet, the distal end having a first nozzle receptacle, a second nozzle receptacle, and a nozzle latch extending outwardly from the distal end and approximately aligned between the first and second nozzle receptacles; and
   a nozzle component removably coupled to the distal end of the atomizer body, the nozzle component comprising a liquid outlet tube having a proximal end configured to couple to the first nozzle receptacle, a gas outlet tube having a proximal end configured to couple to the second nozzle receptacle, and a catch interposed between the liquid outlet tube and the gas outlet tube, and configured to contact the nozzle latch selectively to prevent separation of the nozzle component from the atomizer body, the gas outlet tube and the liquid outlet tube converging into a distal end comprising a nozzle.

2. The device of claim 1, wherein the nozzle component further comprises a gas outlet tube in fluid communication with the gas inlet, and a liquid outlet tube in fluid communication with a container coupled to the container receptacle.

3. The device of claim 1, wherein the nozzle component forms a fluid tight seal with the first and second nozzle receptacles.

4. The device of claim 1, wherein the nozzle latch is resilient.

5. The device of claim 1, wherein the container is threadedly coupled to the container receptacle.

6. A method for manufacturing an atomizer device, the method comprising:
   providing an atomizer body having a proximal end, a distal end, and a container receptacle for receiving a container, the proximal end having a trigger assembly and a gas inlet, the distal end having a first nozzle receptacle, a second nozzle receptacle, and a nozzle latch extending outwardly from the distal end and approximately aligned between the first and second receptacles; and
   providing a nozzle component comprising a liquid outlet tube having a proximal end configured to couple to the first nozzle receptacle, a gas outlet tube having a proximal end configured to couple to the second nozzle receptacle, a catch interposed between the liquid outlet tube and the gas outlet tube, and configured to contact the nozzle latch selectively to prevent separation of the nozzle component from the atomizer body, the gas outlet tube and the liquid outlet tube converging into a distal end comprising a nozzle.

7. The method of claim 6, wherein the nozzle component further comprises a gas outlet tube in fluid communication with the gas inlet and a liquid outlet tube in fluid communication with a fluid container coupled to the container receptacle.

8. The method of claim 6, wherein the nozzle component forms a fluid tight seal with the first and second nozzle receptacles.

9. The method of claim 6, wherein the nozzle latch is resilient.

10. The method of claim 6, wherein the container is threadedly coupled to the container receptacle.

11. A disposable atomizer system, comprising:
    an atomizer body having a gas inlet tube, a liquid inlet tube, a first nozzle receptacle, a second nozzle receptacle, and a nozzle latch extending outwardly from the distal end, and comprising a pair of parallel tubes having a pair of proximal ends, and a pair of distal ends, the proximal ends of the nozzle being removably coupled to the first and second nozzle receptacles of the atomizer body by interference fit, the nozzle further comprising a catch interposed between the pair of tubes, wherein the nozzle latch contacts the catch of the nozzle, and wherein one of the parallel tubes is in fluid communication with the gas inlet tube, and the other parallel tube is in fluid communication with the liquid inlet tube.

12. The system of claim 11, wherein the atomizer body further comprises a trigger assembly.

* * * * *